United States Patent

Kobayashi

[11] 4,228,270
[45] Oct. 14, 1980

[54] POLYBORODIPHENYLSILOXANES

[75] Inventor: Hiroshi Kobayashi, Fuji, Japan

[73] Assignee: Asahi Kasei Kogyo Kabushiki Kaisha, Osaka, Japan

[21] Appl. No.: 969,006

[22] Filed: Dec. 13, 1978

[30] Foreign Application Priority Data

Dec. 14, 1977 [JP] Japan ................ 52-149395
Dec. 20, 1977 [JP] Japan ................ 52-152439

[51] Int. Cl.$^2$ ............................................. C08G 79/08
[52] U.S. Cl. ................................. 528/8; 264/331; 528/5; 528/25; 528/30; 556/402
[58] Field of Search ............... 528/5, 8, 30, 25; 260/606.5 B

[56] References Cited

U.S. PATENT DOCUMENTS

| | | | |
|---|---|---|---|
| 2,517,945 | 8/1950 | Upson | 528/8 |
| 3,161,613 | 12/1964 | Sprung | 528/25 |
| 3,519,670 | 7/1970 | Markovitz | 260/448.2 N |
| 3,519,671 | 7/1970 | Markovitz | 260/448.2 N |
| 4,152,509 | 5/1979 | Yajima et al. | 528/8 |

FOREIGN PATENT DOCUMENTS 1547330 10/1968 France .
45-21597 7/1970 Japan .
255570 1/1970 U.S.S.R. ................ 528/30

Primary Examiner—Melvyn I. Marquis

[57] ABSTRACT

A polyborodiphenylsiloxane having main repeating units of the formula,

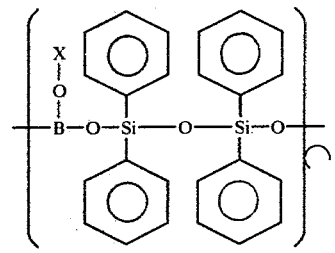

wherein X is a hydrogen atom or

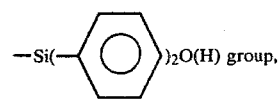

and a weight-average molecular weight of about 800 to about 5,000, and a method of preparing the same, which comprises polycondensing a borodiphenylsiloxanol of the formula,

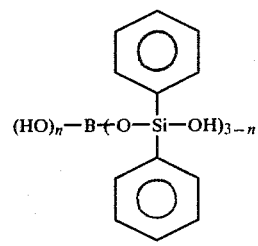

wherein n is zero or one, at a temperature of from about 140° C. to about 400° C. in the absence of a solvent.

7 Claims, 2 Drawing Figures

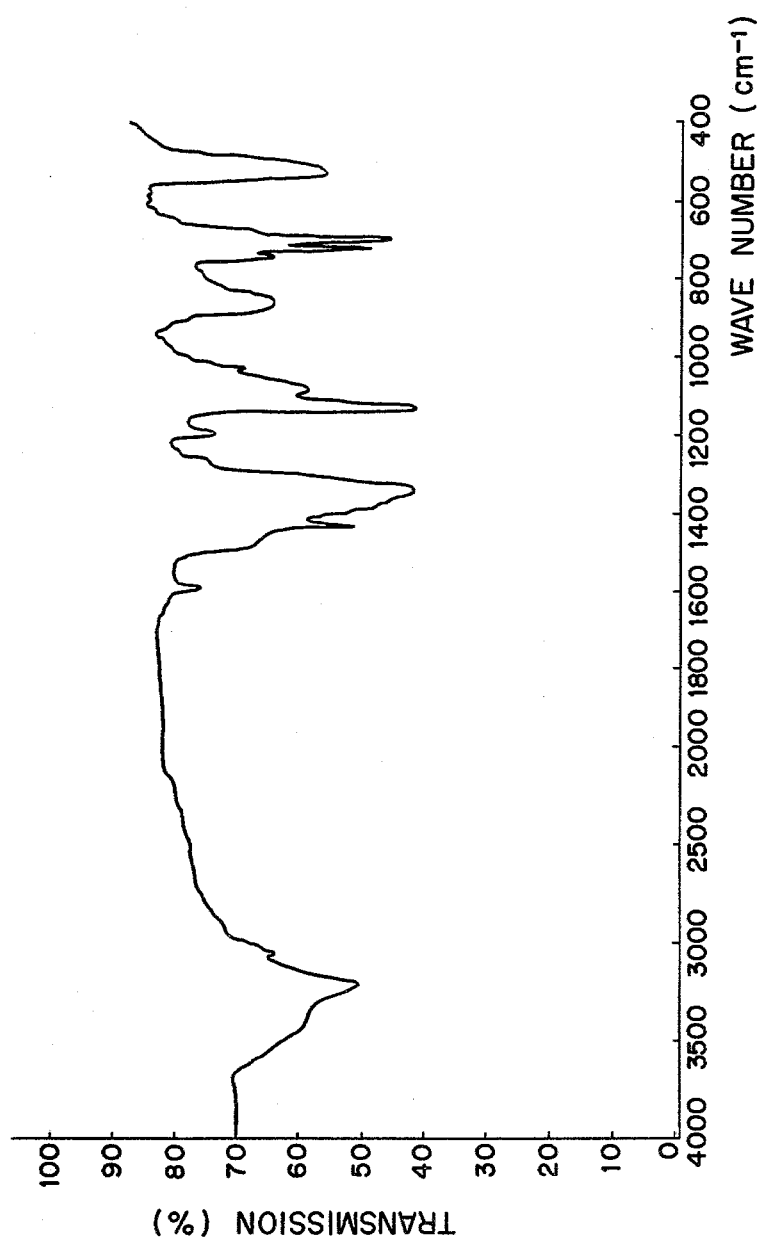

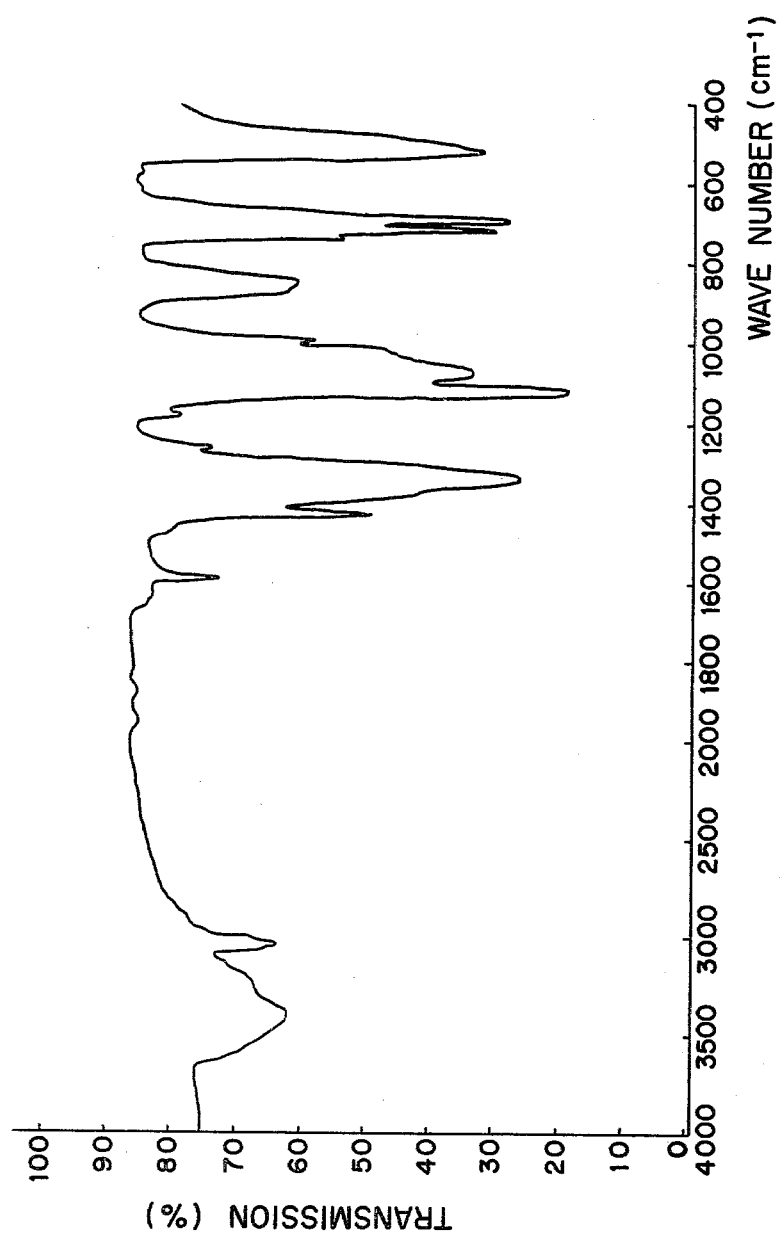

POLYBORODIPHENYLSILOXANES

BACKGROUND OF THE INVENTION

1. Field of the Invention

This invention relates to a novel polyborodiphenylsiloxane and to a novel method of its preparation.

2. Description of the Prior Art

Known conventional polyborosiloxanes are prepared mainly by the following four reactions;

Group (i) Dehydration condensation reaction of boric acid and a silanediol,

Group (ii) Dehydrochlorination condensation reaction of boric acid and a diorganodichlorosilane, Group (iii) Dealkoxylation condensation reaction of boric acid and a diorganodialkoxysilane, and Group (iv) Deesterification condensation reaction of an ester of boric acid and a diorganodialkoxysilane.

The reaction of Group (i) is described, for example, in U.S. Pat. No. 2,517,945, U.S.S.R. Certificate of Inventorship No. 255570, French Patent No. 1547330 and Japanese Patent Publication No. 21597/1970.

SUMMARY OF THE INVENTION

The present invention in one embodiment provides a polyborodiphenylsiloxane having main repeating units of the formula,

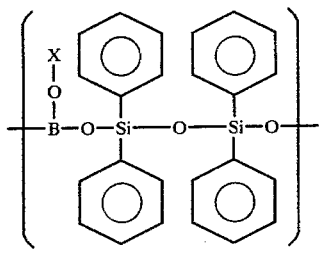

wherein X is a hydrogen atom or

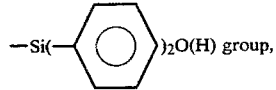

and a weight-average molecular weight of about 800 to about 5,000.

The present invention in another embodiment provides a borodiphenylsiloxanol of the formula,

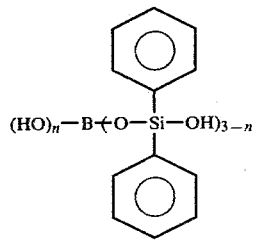

wherein n is zero or one, which can be employed as a starting material for preparing the polyborodiphenylsiloxane as described above.

In a further embodiment, the invention provides a method of preparing the polyborodiphenylsiloxane as described above, which comprises polycondensing the borodiphenylsiloxanol as described above at a temperature of from about 140° C. to about 400° C. in the absence of a solvent.

In an even further embodiment, the invention provides a method of preparing the borodiphenylsiloxanol as described above, which comprises reacting boric acid with diphenylsilanediol at a temperature of from about 80° C. to about 140° C. in the absence of a solvent.

BRIEF DESCRIPTION OF THE ACCOMPANYING DRAWINGS

FIG. 1 is an infrared absorption spectrum of the borodiphenylsiloxanol as obtained in Run No. 2 of Example 1.

FIG. 2 is an infrared absorption spectrum of the polyborodiphenylsiloxane as obtained in Run No. 5 of Example 2.

DETAILED DESCRIPTION OF THE INVENTION

In the preparation of the borodiphenylsiloxanol as described above which can be used as the starting material for preparing the polyborodiphenylsiloxane of this invention the reaction temperature should be higher than the temperature at which the dehydration of only boric acid starts, i.e., about 80° C. and at the same time lower than the temperature at which the dehydration of only diphenylsilanediol starts, i.e., about 120° C. At temperatures between about 80° C. and about 120° C. the dehydration condensation reaction between boric acid and diphenylsilanediol is prior to all other dehydration reactions. When the reaction temperature is above about 120° C., the dehydration condensation of diphenylsilanediol disadvantageously takes place to form cyclic compounds. However, since the rate of the dehydration condensation reaction is remarkably low below about 140° C., i.e., below the melting point of diphenylsilanediol, the temperature of about 120° C. to about 140° C. can also be practically employed in the preparation of the borodiphenylsiloxanol of this invention.

In the present invention the preparation of the borodiphenylsiloxanol is conducted in the absence of any solvent, i.e., in the solid phase since both the dehydration condensation reaction of boric acid and the dehydration condensation reaction of diphenylsilanediol can be easily prevented by controlling the reaction temperature.

The reaction time varies depending upon such factors as the reaction temperature used, the reaction pressure used and the like. It has been found, however, that the reaction time in the range of from about 30 minutes to 3 hours is generally sufficient.

The reaction may be conducted at atmospheric pressure or under reduced pressure, for example, less than about 20 mmHg while removing the water formed during the reaction. The reaction may also be conducted in an inert gas atmosphere such as nitrogen and argon.

The mole ratio of the boric acid to the diphenylsilanediol which can be employed in the preparation of the borodiphenylsiloxanol typically ranges from about ⅓ to about ⅔. If the mole ratio thereof is less than about ⅓, excess diphenylsilanediol remains unreacted and disadvantageously forms cyclic siloxanes when heated up to higher temperatures. Also, if the mole ratio thereof is higher than about ⅔, boric acid is excess and the polyborodiphenylsiloxane which is prepared from the diphenylsilanediol obtained becomes hygroscopic.

The polyborodiphenylsiloxane of this invention can be prepared by polycondensing the borodiphenylsiloxanol at a temperature of from about 140° C. to 400° C. in the absence of an solvent.

The polycondensation may be carried out at atmospheric pressure or under reduced pressure, generally less than 20 mmH while removing the water formed during the polycondensation.

The polycondensation reaction time varies depending upon the temperature used, the pressure used and the like. Typically, the polycondensation reaction time ranges from about 1 to about 5 hours at atmospheric pressure. When the polycondensation is carried out under reduced pressure, the polycondensation time can be further shortened.

The polycondensation may also be conducted in an inert gas atmosphere such as nitrogen and argon.

When the polycondensation temperature employed is from about 300° C. to about 400° C., it is preferred that the polycondensation is carried out in such an inert gas atmosphere as described above or under reduced pressure while removing the water formed during the polycondensation. When the polycondensation is conducted at temperatures above 400° C., the scission of the

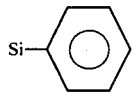

bonds disadvantageously takes place even in an inert gas atmosphere.

It is also preferred that the polycondensation is conducted by two steps, i.e., firstly at a temperature of from about 140° C. to about 250° C. for about one hour and secondly at a temperature of from about 250° C. to about 400° C. for about one hour.

Further, according to the present invention, the polyborodiphenylsiloxane of this invention can be prepared by reacting boric acid with diphenylsilanediol at a temperature of from 80° C. to about 140° C. in the absence of a solvent to form a borodiphenylsiloxanol of the formula,

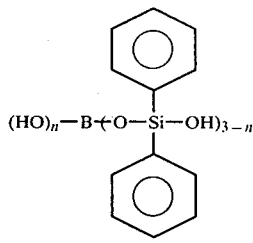

wherein n is zero or one, and polycondensing the borodiphenylsiloxanol at a temperature of about 140° C. to 400° C. in the absence of a solvent. In this method, the same reaction conditions such as the mole ratio of the boric acid to the diphenylsilanediol, the reaction time, the polycondensation time, and the others as described above can also be employed.

The polyborodiphenylsiloxane of this invention has a weight-average molecular weight of from about 800 to 5,000 when measured by gel permeation chromatography. When the weight-average molecular weight of the polyborodiphenylsiloxane becomes more than 5,000 gelation occurs. A preferred weight-average molecular weight thereof ranges from about 800 to about 2,000.

The terminal group of the polyborodiphenylsiloxane is either the hydroxyl group linked with the boron atom or the hydroxyl group linked with the silicon atom of the borodiphenylsiloxanol.

The polyborodiphenylsiloxane of this invention contains more —Si—O—Si— bond units than that obtained by conventional methods, and thus the resistance to hydrolysis of the polyborodiphenylsiloxane of this invention is superior to that obtained by conventional methods. Further, according to the method of this invention, a higher molecular weight polyborodiphenylsiloxane can be obtained. The polyborodiphenylsiloxane of this invention which has a high silicon content is excellent as a precursor for silicon carbide or a sintering auxiliary agent or a binder for ceramics such as silicon carbide.

For example, in employing the polyborodiphenylsiloxane of this invention as a sintering auxiliary agent for ceramics, boric acid, diphenylsilanediol and powdery silicon carbide are thoroughly mixed and the mixture is sintered to form ceramics without isolating the polyborodiphenylsiloxane.

Further, the polyborodiphenylsiloxane of this invention is useful as a curing agent for epoxy resins, a surface treating agent for glass fibers or carbon fibers and an additive for organic or inorganic lenses.

The characteristic feature of the polyborodiphenylsiloxane of this invention is that —Si—O— bond units form a chain. This is the most different point in which the polyborodiphenylsiloxanes according to conventional methods differ from the polyborodiphenylsiloxane according to this invention. It is most appropriate that the polyborodiphenylsiloxane and the borodiphenylsiloxanol of this invention may be specified by the ratio of intensities of absorptions in their infrared absorption spectra. More specifically, the infrared absorption due to the —B—O—(Si) bond and that due to the —Si—O—(Si,B) bond appear at 1340 cm$^{-1}$ and 1080 cm$^{-1}$, respectively. The infrared absorption due to the mono-substituted benzene appears at 695 cm$^{-1}$. When the ratio of intensities of the absorptions at 1340 cm$^{-1}$ to at 695 cm$^{-1}$ and that of intensities of the absorptions at 1080 cm$^{-1}$ to at 695 cm$^{-1}$ are indicated as $\delta 1340$ cm$^{-1}/\delta 695$ cm$^{-1}$ and $\delta 1080$ cm$^{-1}/\delta 695$ cm$^{-1}$, respectively, the polyborodiphenylsiloxane and the borodiphenylsiloxanol of this invention can be specified by these ratios, that is, the amounts of the —B—O—Si bond and the —Si—O—Si bond can be quantitatively determined. In the present invention these values showing the ratios of intensities of the absorptions in the infrared absorption spectra are calculated from the infrared absorption spectra of the polyborodiphenylsiloxane and the borodiphenylsiloxanol measured by the conventional KBr method. With regard to the borodiphenylsiloxanol, the ratio $\delta 1340$ cm$^{-1}/\delta 695$ cm$^{-1}$ approximates to 1.2 and the ratio $\delta 1084$ cm$^{-1}/\delta 695$ cm$^{-1}$ approximates to 0.5. With regard to the polyborodiphenylsiloxane, the ratio $\delta 1340$ cm$^{-1}/\delta 695$ cm$^{-1}$ approximates to 0.8 and the ratio $\delta 1080$ cm$^{-1}$ approximates to 0.9.

The following Examples are given to illustrate the present invention more specifically. However, it should be understood that the invention is in no way limited by these Examples.

EXAMPLE 1

Preparation of Borodiphenylsiloxanols

Boric acid and diphenylsilanediol in an amount as set forth in Table I were placed in an agate mortar, thoroughly pulverized and mixed. The mixture was charged in a flask and heated from 25° C. to 100° C. over 20 minutes and further at 100° C. for 2 hours in an open system to give a white solid product. The results are shown in Table I below.

TABLE I

| Run No. | Boric Acid (g) | Diphenyl-silanediol (g) | Mole Ratio of Boric Acid to Diphenyl-silanediol | Borodiphenylsiloxanol Absorption Spectrum | | Rate of Dehydration* [Theoretical Value]** (%) |
|---|---|---|---|---|---|---|
| | | | | $\delta 1340\,cm^{-1}$ / $\delta 695\,cm^{-1}$ | $\delta 1080\,cm^{-1}$ / $\delta 695\,cm^{-1}$ | |
| 1 | 9.3 | 64.5 | 1/3 | 1.11 | 0.42 | 6.0 [5.1] |
| 2 | 14.0 | 64.5 | 1.5/3 | 1.13 | 0.55 | 7.1 [7.3] |
| 3 | 18.6 | 64.5 | 2/3 | 1.13 | 0.56 | 10.0 [8.29] |

*Measured by thermal gravimetric analysis. Temperature was raised from 40° C. to 120° C. at a rate of 5° C. per minute
**Theoretical value was calculated on the assumption that the dehydration of boric acid to form metaboric acid and the reaction of metaboric with diphenylsilanediol to form borodiphenylsiloxanol took place.

In the infrared absorption spectrum of the borodiphenylsiloxanol of Run No. 2 as shown in FIG. 1, characteristic absorptions based on —B—O—(Si), —Si—O—(Si,B) and

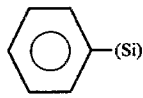

were observed at $1340\,cm^{-1}$, $1080\,cm^{-1}$ and $695\,cm^{-1}$, respectively.

EXAMPLE 2

Preparation of Polyborodiphenylsiloxanes

The borodiphenylsiloxanol as set forth in Table II was polycondensed in the absence of a solvent under the conditions as set forth Table II to give a colorless transparent resinous product. The results are shown in Tabe II below.

EXAMPLE 3

Preparation of Polyborodiphenylsiloxane

The borodiphenylsiloxanol obtained in Run No. 2 of Example1 was polycondensed in the absence of a solent in a nitrogen atmosphere at 250° C. for one hour and further at 400° C. for one hour while removing the water formed from the reaction system. As the result, there was obtained a slightly pale brown transparent resinous product having a weight-average molecular weight of about 1,500 (maximum: 2,000) as measured by gel permeation chromatography, a ratio $\delta 1340\,cm^{-1}/\delta 695\,cm^{-1}$ of 0.80 and a ratio $\delta 1080\,cm^{-1}/\delta 695\,cm^{-1}$ of 0.95.

EXAMPLE 4

Use of Polyborodiphenylsiloxanes 5 g of the polyborodiphenylsiloxane in Run No. 2 of Example 2 and 45 g of powdery silicon carbide having passed through a 300 mesh Tyler standard sieve were added to 70 ml of tetrahydrofuran, thoroughly mixed and dried in a drier by removing the tetrahydrofuran. The mixed powder before completely dried was charged in a mold of $10\times50\,mm^2$ and press-molded under a pressure of 500 Kg/cm$^2$ to give a molded article. The article thus obtained was placed in an aluminum Tammann tube and sintered in an argon atmosphere by raising the temperature from 25° C. to 1,700° C. at a rate of 100° C. per hour.

The sintered shaped article obtained had a bulk density of 2.65 g/cm$^3$ and a flexural strength of 14 Kg/mm$^2$.

TABLE II

| Run No. | Borodiphenyl-siloxanol (Run No. of Example 1) | Polycondensation Temperature & Time °C. (hour) | Polyborodiphenylsiloxane Infrared Absorption Spectrum | | Weight-Average Molecular Weight* (Maximum) |
|---|---|---|---|---|---|
| | | | $\delta 1340\,cm^{-1}$ / $\delta 695\,cm^{-1}$ | $\delta 1080\,cm^{-1}$ / $\delta 695\,cm^{-1}$ | |
| 1 | 1 | 200(1), 330(1) | 0.78 | 0.71 | 1,000(1,200) |
| 2 | 2 | 200(1), 330(1) | 0.90 | 0.93 | 1,000(1,200) |
| 3 | 3 | 200(1), 330(1) | 0.82 | 0.87 | 1,000(1,200) |
| 4 | 2 | 200(2) | 0.97 | 0.71 | 900(1,000) |
| 5 | 2 | 240(2) | 0.97 | 0.78 | 900(1,200) |
| 6 | 2 | 200(1), 400(1)** | 0.75 | 0.98 | 1,500(2,000) |
| 7 | 3 | 200(1), 400(1)** | 0.80 | 0.95 | 1,500(2,000) |

*In a column having a length of 90 cm and an inner diameter of 2.5 cm and packed with BIOBEAS SX-2 was introduced a 5 cc tetrahydrofuran solution dissolving therein 30 mg of the product at a flow rate of 2.2 cc per minute and its refractive index was measured by a refractometer. The maximum molecular weight and the weight-average molecular weight were obtained by the counts of the fractions.
**In Run Nos. 6 and 7 the step of the polycondensation at 400° C. for one hour was conducted under a reduced pressure of 10 mmHg. In the other Runs the polycondensation was conducted at atmospheric pressure.

In the infrared absorption spectrum of the polyborodiphenylsiloxane of Run No. 5 of Example 2 as shown in FIG. 2, the same characteristic absorptions as in FIG. 1 were observed.

Further, when the article was oxidized at 1,400° C. in an oxidizing atmosphere, the bulk density and the flexural strength were 2.50 g/cm$^2$ and 15 Kg/mm$^2$, respectively.

The amount increased by oxidation at 1,400° C. after 40 hours was 20 mg/cm².

Also, the polyborodiphenylsiloxane obtained in Run No. 1 of Example 2 was press-molded and sintered up to a temperature of 1,700° C. in the same manner as described above.

The sintered shaped article had a bulk density of 2.60 g/cm³ and a flexural strength of 14 Kg/mm².

The amount increased by oxidation at 1,400° C. after 40 hours was 15 mg/cm².

EXAMPLE 5

Use of Polyborodiphenylsiloxane 4.6 g of boric acid, 32.4 g of diphenylsilanediol and 350 g of silicon carbide having passed through a 300 mesh Tyler standard sieve were pulverized and mixed in the dry state for 24 hours. The mixture was moded into a shaped article at 100° C. under a pressure of 200 Kg/cm² for 15 minutes. The article thus obtained was sintered up to a temperature of 1,700° C. in the same manner as in Example 4.

The sintered shaped article had a bulk density of 2.70 g/cm³ and a flexural strength of 16 Kg/mm².

The amount increased by oxidation at 1,400° C. after 40 hours was 15 mg/cm².

EXAMPLE 6

Use of Polyborodiphenylsiloxane

To 100 g of an epoxy resin having a melting point of 140° C. and an epoxy equivalent of 2,500 (trademark "AER 669", manufactured by Asahi Kasei Kogyo Kabushiki Kaisha) were added 20 g of the polyborodiphenylsiloxane obtained in Run No. 2 of Example 2, mixed under heating at 150° C. and left to stand. The mixture was completely hardened for 5 minutes. The article hardened had a Rockwell hardness of M-110 and its adhesive to glass was 100 according to the crosscut test (remainder/100) ("Testing Methods for Paints" by Japan Association of Investigation of Industrial Standards).

While the invention has been described in detail and with reference to specific embodiments thereof, it will be to one skilled in the art that various changes and modifications can be made therein without department from the spirit and scope thereof.

What is claimed is:

1. A polyborodiphenylsiloxane having main repeating units of the formula,

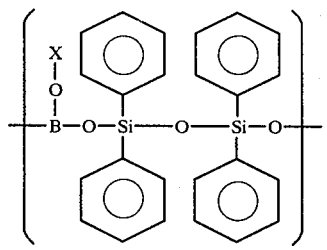

wherein X is a hydrogen atom or

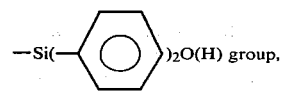

and a weight-average molecular weight of about 800 to about 5,000.

2. The polyborodiphenylsiloxane of claim 1, wherein the weight-average molecular weight ranges from about 800 to about 2,000.

3. A method of preparing the polyborodiphenylsiloxane of claim 1, which comprises polycondensing a borodiphenylsiloxanol of the formula,

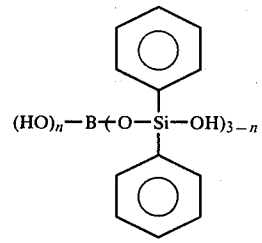

wherein n is zero or one, at a temperature of from about 140° C. to about 400° C. in the absence of a solvent.

4. The method of claim 3, wherein the polycondensation is carried out at a temperature of from about 140° C. to about 250° C. for about one hour and further at a temperature of from about 250° C. to about 400° C. for about one hour.

5. The method of claim 3, wherein the polycondensation is carried out in an inert gas atmosphere.

6. The method of claim 3, wherein the polycondensation is carried out under reduced pressure.

7. The method of preparing the polyborodiphenylsiloxane of claim 1 which comprises reacting boric acid with diphenylsilanediol in a mole ratio of the boric acid to the diphenylsiloxanediol of from about ⅓ to about ⅔ at a temperature of from about 80° C. to about 140° C. in the absence of a solvent to form a borodiphenylsiloxanol of the formula,

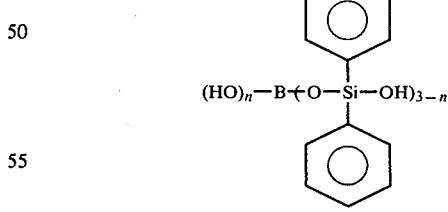

wherein n is zero or one, and polycondensing the borodiphenylsiloxanol at a temperature of about 140° C. to about 400° C. in the absence of a solvent.

* * * * *